United States Patent [19]

Perry

[11] Patent Number: 5,158,458
[45] Date of Patent: Oct. 27, 1992

[54] SYSTEM FOR DRIVING AND TIGHTENING COMPONENTS IN A PROSTHODONTIC RESTORATION

[76] Inventor: William L. Perry, 1517 Live Oak, Irving, Tex. 75061

[21] Appl. No.: 720,948

[22] Filed: Jun. 25, 1991

[51] Int. Cl.$^5$ ............................................. A61C 3/00
[52] U.S. Cl. ..................................... 433/141; 81/471; 433/174
[58] Field of Search .................. 433/141, 174; 81/467, 81/471, 473, 474, 475, 476

[56] References Cited

U.S. PATENT DOCUMENTS

| | | | |
|---|---|---|---|
| 881,075 | 3/1908 | Hosking | 81/471 |
| 3,191,486 | 6/1965 | Gibbens | 81/471 |
| 3,279,286 | 10/1966 | Larson | 81/474 |
| 4,177,562 | 12/1979 | Miller et al. | 433/174 |
| 4,215,600 | 8/1980 | Kesselman | 81/471 |
| 4,687,392 | 8/1987 | Bidwell | 81/475 |
| 4,833,951 | 5/1989 | Karcher et al. | 81/471 |
| 4,976,617 | 12/1990 | Carchidi | 433/141 |

Primary Examiner—John J. Wilson
Attorney, Agent, or Firm—David H. Judson

[57] ABSTRACT

A system for driving and tightening components in a dental prosthodontic restoration. The system comprises at least a first driver having a body portion and a shank portion depending from the body portion, the body portion including a socket and a bore axially disposed through the body portion and opening through to the socket, the shank portion having a predetermined driver structure at one end. The system includes at least a first torque element comprising an outer member and an inner member, the inner member aligned with respect to the outer member and attached thereto by one or more spokes, the outer member having a predetermined geometry to enable the outer member to be received in the socket of the driver. A mandrel is also provided and includes a first portion received in the inner member of the torque element and a second portion received in the bore when the mandrel, the torque element and the driver are assembled together. Upon rotation of the mandrel, the inner member of the torque element rotates with respect to the outer member of the torque element only while the spokes are intact. The number of spokes and the placement of the spokes relative to the inner and outer members of the torque element are predetermined such that upon rotation of the mandrel the spokes remain intact provided the torque applied to the mandrel is below a predetermined level.

10 Claims, 1 Drawing Sheet

SYSTEM FOR DRIVING AND TIGHTENING COMPONENTS IN A PROSTHODONTIC RESTORATION

TECHNICAL FIELD

The present invention relates generally to restorative dentistry and more particularly to a system for driving and tightening components used in a dental prosthodontic restoration.

BACKGROUND OF THE INVENTION

Prosthodontic restorative systems and techniques are well-known in the prior art. For partially or fully edentulous patients, a dental implant fixture is implanted in a cylindrical bore made in the alveolar ridge crest of a patient's jawbone after the gum tissue has been displaced. The fixture typically includes an internally-threaded cylindrical socket which receives one or more components used for attaching a permanent dental restoration to the fixture. The components typically include an abutment base in the form of a short tubular body having a transverse wall at a first end thereof shaped to mate with the gingival aspect of a transverse surface of the implant fixture. The abutment base has a bore therethrough for receiving an abutment screw used to retain the abutment base to the fixture. A coping is retained in the abutment screw using a coping screw. A dental restoration, in the form of an anatomical overlay, is adapted to be fabricated to the coping. One such system is shown in U.S. Pat. No. 4,988,298 to Lazzara et al.

The various components of the dental prosthodontic restoration are typically driven and tightened with respect to the implant mixture or each other using a plurality of different drivers, one for each type of component. The prosthodontist manipulates the drivers manually or through the use of an automatic device. One such automatic device is marketed by Nobel Industries Sweden and includes a torque control mechanism to insure that components are tightened to their optimum torque.

Precise and complete tightening of the components in a restoration is often difficult to achieve manually. Thus, the components often loosen and back-out of their fittings, requiring repeated office visits for retightening. While automatic devices generally overcome this problem, such devices are costly and somewhat cumbersome to use. Moreover, the accuracy of such devices will degrade over time by wear, tear and adverse effects of sterilization.

There is therefore a need to provide a new system for driving components used in a dental prosthodontic restoration that overcomes these and other problems of the prior art.

BRIEF SUMMARY OF THE INVENTION

It is an object of the present invention to provide a system for driving components of a dental restoration system that precisely and reproducibly tightens components to a specified toque in a simple and cost effective way.

It is a further object of the invention to provide such a system that is simple and easy-to-use, and that can be driven manually (e.g., by finger grip or rachet) or automatically (e.g., by a handpiece).

It is still another object to provide a system for driving components in a dental restoration system that can be used with a variety of different makes and styles of component parts.

It is yet a further object to provide such a system that has little or no maintenance and which includes disposable elements.

These and other objects of the invention are provided in a system for driving and tightening components used in a dental prosthodontic restoration comprising a plurality of interchangeable drivers and a plurality of torque elements each having predetermined torque ratings. In the preferred embodiment, the system includes at least a first driver having a body portion and a shank portion depending from the body portion, the body portion including a socket and a bore axially disposed through the body portion and opening through to the socket, the shank portion having a predetermined driver structure at one end. The system includes at least a first torque element comprising an outer member and an inner member, the inner member aligned concentrically with respect to the outer member and attached thereto by one or more spokes, the outer member having a predetermined geometry to enable the outer member to be received in the socket of the driver. A mandrel is also provided and includes a first portion received in the inner member of the torque element and a second portion received in the bore when the handpiece, the torque element and the driver are assembled together. Upon rotation of the mandrel, the inner member of the torque element rotates with respect to the outer member of the torque element only if the spokes are intact, i.e., unbroken. The number of spokes and the placement of the spokes relative to the inner and outer members of the torque element are predetermined such that upon rotation of the handpiece the spokes remain intact provided the torque applied to the handpiece is below a predetermined level.

The mandrel is driven either manually through the use of a finger grip or rachet, or automatically through the use of a power-driven handpiece attached thereto. Thus, according to the invention a plurality of interchangeable drivers and torque elements are provided and these drivers and torque elements are sized for various components and/or applications. The dental professional merely selects the appropriate driver and torque element for the specific task.

The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which.

DETAILED DESCRIPTION

The driver system of the present invention is useful in single tooth, partially-edentulous, fully-edentulous or fixed-removable restorations. For purposes of simplicity, however, the following description is limited to describing the invention in the context of a single tooth restoration. Such a prosthodontic restoration includes a dental implant fixture which is implanted in a cylindrical bore made in the alveolar ridge crest of a patient's jawbone after the gum tissue has been displaced. A coronal end of the fixture has at its gingival aspect a transverse surface that is substantially flush with the alveolar ridge crest after the fixture is implanted. The implant fixture has an internally-threaded socket. After the implant fixture has osseointegrated with the jawbone of the patient, an abutment is fitted to the fixture through an opening in the overlying gum tissue. The abutment typically has a female indentation (i.e., a socket) at its superior end, and either a male projection or female indentation at its inferior end adapted to mate with a corresponding indentation or socket of the implant fixture. A central bore passes through the abutment for receiving an abutment screw secures the abutment base to the implant fixture. The abutment screw typically has an externally threaded shaft intended to mate with the internally-threaded socket in the implant fixture. When the abutment is the so-called "standard" type, a castable or precision-milled coping is normally secured to the abutment screw using a coping screw. No coping is required when a "direct" abutment is used.

The various components of the dental restoration, i.e., the abutment base, the abutment screw, the coping and the coping screw, must be sufficiently and adequately tightened to prevent one or more of these components from loosening or otherwise "backing-out." Further, over-tightening of any such component could cause premature breakage. The amount of torque which must be applied by the dental prosthodontist or other practitioner varies considerably because of the differences in the sizes, weights and configurations of the components. The present invention provides a universal driver system for use in driving and tightening all such components regardless of size, weight, manufacturer or other physical differences of such components of a dental prosthodontic restoration.

Figure 1:
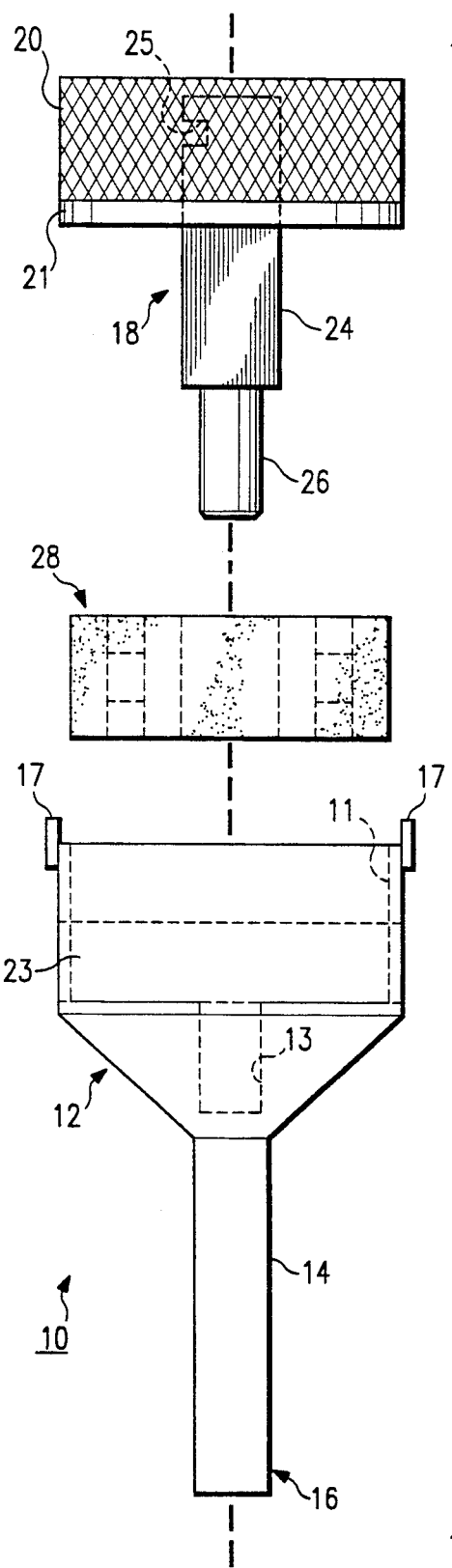
FIG. 1 is an exploded elevational view showing the various elements of the driver system according to the teachings of the present invention.
Figure 2A:
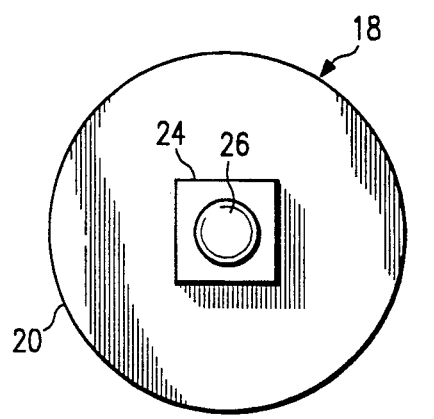
FIGS. 2A–C are plan views of the finger grip, the torque element and the driver element of the driver system shown in FIG. 1.
Figure 2B:
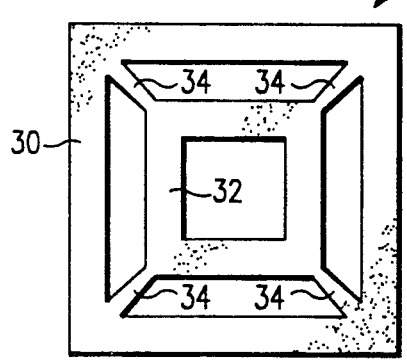
Figure 2C:
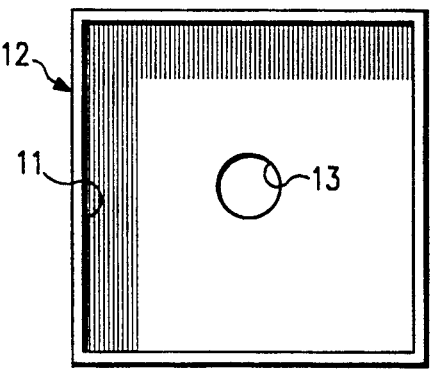

The system includes a plurality of interchangeable drivers, one of which is designated by the reference numeral 10 in FIG. 1. Driver 10 is also shown in plan view in FIG. 2C. Each driver includes a body 12 at its superior aspect which, for exemplary purposes only, is shown as being square in shape. The body 12 includes a retaining socket 11 and a central bore 13 for the purposes to be described. A shank 14 is attached to or otherwise integrally-formed with the body and terminates in an end portion 16. The actual construction of the end portion 16 of the shank 14 depends on the type of component of the restoration being tightened. In FIG. 1, the end portion is formed in the shape of a screw driver for tightening an abutment screw (not shown). A different size head would, of course, be required if the driver were being used to tighten a coping screw or other type of fitting or retaining component. A complete set of interchangeable drivers is thus provided for each type and/or size of component of the restoration that is required to be tightened by the dental professional.

The system further includes at least one mandrel 18, shown partly in phantom in FIG. 1, which has first and second portions 24 and 26. The first portion 24 of the mandrel 18 is preferably square in shape and has a notch 25 formed adjacent the top thereof for enabling the mandrel to be retained in a finger grip 20. Alternatively, the mandrel is retained in a handpiece of a power driver (such as a drill) or a rachet. The finger grip 20 includes a serrated outer periphery. The second portion 26 of the mandrel 18 is preferably circular in shape and is adapted to be received in the central bore 13 of the driver body. The shape of the second portion 26 must be the same as the shape of the central bore (of the driver 10), however, the precise shape is not limited to the round construction shown in the example.

The driver system further includes a set of torque elements, one of which is designated generally by the reference numeral 28 and shown in elevation in FIG. 1. The torque element 28 is shown in plan view in FIG. 2B. Element 28 comprises two members, an outer member 30 and an inner member 32, with the inner member 32 aligned concentrically with respect to the outer member by one or more spokes 34. Preferably, the torque element 28 is formed of a rigid plastic or rubber material. As force is applied to rotate the inner member 32 about its vertical axis, the spokes 34 are flexed to enable the inner member 32 to rotate within the outer member 30. According to the invention, the spokes 34 are fabricated to break when a predetermined torque has been applied thereto. The predetermined amount of torque depends on a number of factors including the number, the position and the thickness of the spokes, as well as the properties of the material front which the element 28 is fabricated. A set of torque elements 28 are provided with the set of drivers 10. These elements are provided with predetermined torque settings for the various types of components that must tightened in the restoration. The torque elements are preferably color-coded or otherwise marked with appropriate indicia to enable the dental professional to quickly retrieve the properly-sized element for the specific component and/or manufacturer.

Referring back to the drawings, in one embodiment the element 28 is placed into the torque element retaining socket 11 and thus locks into the superior aspect of the driver by virtue of having the same geometrical configuration. Alternatively, a slot 23 is formed in the driver 10 for enabling the element to be slid into the socket 13 and retained in the socket (in which case the socket need not open out from the superior aspect of the driver). Thus the torque element 13 is either dropped or laterally slid into the socket. Of course, the shape of the outer member 30 of the torque element must match the shape of the socket 11. The mandrel 18 is received in the driver after the torque element 28 is supported in the socket 11. In particular, the first portion 24 of the mandrel is received in the inner member 32 of the torque element 28. The second portion 26 of the shaft is received snugly in the central bore 13 of the driver to prevent lateral or vertical loading on the torque element 28. As previously noted, the shape of the first portion 24 of the mandrel 22 must match the shape of the inner periphery of the inner member 32 of the anti-torque element 28.

As shown in FIG. 1, the driver body 12 preferably includes flanges 17 for receiving the outer bottom side edges 21 of the finger grip 20. Side edges 21 are smooth rather than serrated. Conversely, side edges 21 may include depending flanges (in which case the flanges 17 are omitted). All vertical pressure is transferred to the driver 10, and the torque element 28 reacts only to the rotational force applied to the finger grip. The contact points between the driver and the finger grip are smooth but stable such that no rotational forces are applied except through a torque element 28 having intact spokes.

In operation, the dental professional selects the appropriate driver and/or torque element depending on the component to be tightened. The driver system is then assembled as shown in FIG. 1 and used to drive and tighten the specific component. If too much torque is applied for the specific application, the spokes in the torque element will break, but the dental professional will then be assured that the optimal torque has been applied to the component. Torque elements having broken spokes are then discarded.

The driver system precisely and reproducibly tightens components to a specified torque in a simple and cost effective way. The system is composed of interchangeable drivers which can be manually or automatically driven. A driver is made for each specific application indication. The mandrel or finger grip is generic and can be used with all drivers. The torque elements are made specific to the application and desired torque. Hence, a specific element is used to obtain a specific torque. Aside from the predictability, reproducibility, simplicity, and cost effectiveness of this system, no maintenance is required. As there are no moving or technically sensitive parts, wear and sterilization will not alter the function or precision. The torque element is the precision component and it is disposable.

It should be appreciated by those skilled in the art that the specific embodiments disclosed above may be readily utilized as a basis for modifying or designing other structures for carrying out the same purposes of the present invention. For example, the torque element may be integrally formed with the body portion of the driver, and one or more shank portions (having different ends) can then be interchanged therewith. The torque element may be formed with the mandrel directly. Yet another alternative involves inverting the driver 10 and using the inverted driver as a mandrel; in such case the mandrel 18 (of FIG. 1) is provided with a fitting (male or female) for driving the restoration component. The system is universally applicable and useful for driving and tightening components in other applications besides dental prosthodontic restorations. It should also be realized by those skilled in the art that such equivalent constructions do not depart from the spirit and scope of the invention as set forth in the appended claims.

What is claimed is:

1. A system for driving and tightening components in a dental prosthodontic restoration, comprising:
   at least a first driver having a body portion and a shank portion depending from the body portion, the body portion including a socket and a bore axially disposed through the body portion and opening through to the socket, the shank portion having a predetermined driver structure at one end;
   at least a first torque element comprising an outer member and an inner member, the inner member aligned concentrically with respect to the outer member and attached thereto by one or more spokes, the outer member having a predetermined geometry to enable the outer member to be received in the socket of the driver; and
   a mandrel having a first portion received in the inner member of the torque element and a second portion received in the bore when the mandrel, the torque element and the driver are assembled together;
   wherein upon rotation of the mandrel, the inner member of the torque element rotates with respect to the outer member of the torque element while the spokes are intact.

2. The system as described in claim 1 wherein the number of spokes and the placement of the spokes relative to the inner and outer members of the torque element are predetermined such that upon rotation of the mandrel the spokes remain intact provided the torque applied to the mandrel is below a predetermined level.

3. The system as described in claim 1 further including:
   a second driver having a body portion and a shank portion depending from the body portion, the shank portion of the second driver having a predetermined driver structure at one end that differs from the predetermined driver structure at the end of the first driver.

4. The system as described in claim 1 further including:
   a second torque element comprising an outer member and an inner member, the inner member aligned concentrically with respect to the outer member and attached thereto by one or more spokes, wherein the physical properties of the spokes in the second torque element differ from the physical properties of the spokes in the first torque element.

5. The system as described in claim 4 wherein the first and second torque elements are provided in different colors.

6. The system as described in claim 1 further including means for driving the mandrel.

7. The system as described in claim 6 wherein the means for driving the mandrel is a finger grip attached to the handpiece.

8. The system as described in claim 6 wherein the means for driving the mandrel is a handpiece attachable to a power driver device.

9. The system as described in claim 1 wherein the body portion includes a slot for receiving the first torque element.

10. A system for driving and tightening components in a dental prosthodontic restoration, comprising:
    a first driver having a body portion and a shank portion depending from the body portion, the body portion including a socket and a bore axially disposed through the body portion and opening through to the socket, the shank portion having a predetermined driver structure at one end;
    a second driver having a body portion and a shank portion depending from the body portion, the shank portion of the second driver having a predetermined driver structure at one end that differs from the predetermined driver structure at the end of the first driver;
    a first torque element comprising an outer member and an inner member, the inner member aligned concentrically with respect to the outer member and attached thereto by one or more spokes, the outer member having a predetermined geometry to enable the outer member to be received in the socket of the driver;

a second torque element comprising an outer member and an inner member, the inner member aligned concentrically with respect to the outer member and attached thereto by one or more spokes, wherein the physical properties of the spokes in the second torque element differ from the physical properties of the spokes in the first torque element;

a mandrel having a first portion received in the inner member of a selected one of the first or second torque elements and a second portion received in the bore of a selected one of the first or second driver when the handpiece, the selected torque element and the selected driver are assembled together; and means for driving the mandrel.

* * * * *